US006414033B1

(12) United States Patent
Sceusa

(10) Patent No.: US 6,414,033 B1
(45) Date of Patent: Jul. 2, 2002

(54) DRUG DOSAGE FORM BASED ON THE TEORELL-MEYER GRADIENT

(75) Inventor: Nicholas Sceusa, New York, NY (US)

(73) Assignee: Gelsus Research and Consulting, Inc., New York, NY (US)

( * ) Notice: Subject to any disclaimer, the term of this patent is extended or adjusted under 35 U.S.C. 154(b) by 0 days.

(21) Appl. No.: 09/381,469

(22) PCT Filed: Dec. 6, 1999

(86) PCT No.: PCT/US99/00205

§ 371 (c)(1),
(2), (4) Date: Sep. 20, 1999

(87) PCT Pub. No.: WO99/34751

PCT Pub. Date: Jul. 15, 1999

Related U.S. Application Data

(60) Provisional application No. 60/070,600, filed on Jan. 6, 1998.

(51) Int. Cl.[7] ...................... A61K 31/135; A61K 31/04; A61K 47/00
(52) U.S. Cl. ........................ 514/648; 514/653; 514/727; 514/730; 514/741; 514/772; 514/784; 514/788
(58) Field of Search .................................. 514/648, 653, 514/727, 730, 741, 772, 784, 788

(56) References Cited

U.S. PATENT DOCUMENTS

| | | | |
|---|---|---|---|
| 3,039,922 A | 6/1962 | Berger et al. ................ | 514/357 |
| 5,976,556 A | * 11/1999 | Norton et al. ............... | 424/401 |

FOREIGN PATENT DOCUMENTS

| | | |
|---|---|---|
| GB | 2255892 | 11/1992 |
| WO | WOX 9103236 | 3/1991 |

OTHER PUBLICATIONS

Remington: The Science and Practice of Pharmacy (19th Ed. 1995), pp. 225–27, 229,230,335,707–17.*

Schurmann, et al., The buccal absorption of atenolol and propranolol, and their physicochemical characteristics, J. Clin. Pharmacol., 1977; 4(5):655–656.

Nair, et al., Biomembrane Permeation of Nicotine: Mechanistic Studies with Porcine Mucosae and Skin, J. Pharm. Sci., 1997; 86(2): 257–262.

Al–Sayed–Omar, et al., Influence of pH of the buccal absorption of morphine sulphate and its major metabolite, morphine–3–glucuronide, J. Pharm. Pharacol., 1987;39: 934–935.

Teorell, Transport Phenomena in Membranes Eights Spiers Memorial Lecture, Discussions Faraday Soc., 1956; 21(9):305–369.

Sieg, et al., Vehicle Effects on Ocular Drug Bioavailability II: Evaluation of Pilocarpine, Journal of Pharmaceutical Sciences, 1977; 66(9):1222–1228.

Odumosu, et al., The Buccal Absorption of Ascorbic Acid and its Passage through Lipoid Membrane, Internat. J. Vit. Nutr. Res., 1977; 47(2):135–144.

* cited by examiner

*Primary Examiner*—Sabiha Qazi
*Assistant Examiner*—Frank Choi
(74) *Attorney, Agent, or Firm*—Browdy and Neimark

(57) ABSTRACT

A method for delivery of pharmaceutically effective amounts of drugs and therapeutic ions is disclosed. More particularly, a method of formulating a dosage form that will move drugs, pro-drugs or therapeutic ions in either cationic or anionic form between voltaic cell compartments of the human body, such as from the mouth into the nasopharyngeal area or into the lung is set forth. The method utilizes naturally occurring concentration gradients in the form of concentration cells, which are constituents of the anatomy. A dosage formulation designed in consideration of naturally occurring pH gradients, i.e., Teorell-Meyer gradients, and a method of treatment by delivering a pharmaceutically effective amount of ions or drugs using the formulation designed in consideration of Teorell-Meyer gradients, is also described.

30 Claims, 1 Drawing Sheet

THE MOUTH AND NOSE REPRESENTED AS AN ELECTROPHORETIC SHEET

DRUG DOSAGE FORM BASED ON THE TEORELL-MEYER GRADIENT

This application is a 371 of PCT/US99/00205.

This application is based on a provisional patent application 60/070,600, filed under 37 C.F.R. § 1.53(b)(2) on Jan. 6, 1998, the disclosure and information therein is incorporated herein by reference.

FIELD OF THE INVENTION

This invention relates to a method for delivery of pharmaceutically effective amounts of drugs and therapeutic ions. More particularly, this invention relates to a method of formulating a dosage form that will move drugs, pro-drugs or therapeutic ions in either cationic or anionic form between voltaic cell compartments of the human body, such as from the mouth into the naso-pharyngeal area or into the lung. This invention utilizes the naturally occurring concentration gradients in the form of concentration cells, which are constituents of the anatomy. This invention also relates to a dosage formulation designed in consideration of naturally occurring pH gradients, i.e., Teorell-Meyer gradients, and a method of treatment by delivering a pharmaceutically effective amount of ions or drugs using the formulation designed in consideration of Teorell-Meyer gradients.

BACKGROUND

A new method for delivery of ions and drugs in ionic form is disclosed, including dosage forms designed according to the method of this invention. This dosage form represents an active dosage form that uses charge as a driving principle and is a complete departure from passive dosage forms, The dosage form will be able to move either cations or anions by taking advantage of the naturally occuring concentration gradients that exist in concentration "cells" of the anatomy. One such concentration cell exists between from the mouth into the naso-pharyngeal area, trachea and possibly the lung. It is formed by the buccal cavity, the epiglottis and the naso-pharynx. By either raising or lowering the pH of the mouth to a suitable extent, by using a dosage form buffered at a correct pH, the ion or ionized drug or pro-drug will be moved electro-osmotically in accordance with Teorell-Meyer flux gradients.

The design of dosage forms according to this invention that are capable of moving ions, ionized drugs or carrier ions from one physiological compartment to another (defining a "cell"), in a pH dependent manner, derives mathematically from the Teorell-Meyer Theory. See, Teorell, T., Discussions Faraday Soc., 1956, 21(9), 305–369. The derivation according to this invention predicts that a dosage form buffered at the correct pH will be able to move either the desired positive or negative ions from compartment A to compartment B in an pH dependent osmo-electrophoretic manner, provided a flux gradient exists between two and possibly more compartments. Examples of such compartments are: mouth—nose; vagina—uterous—Fallopian tubes; outer and inner ear; and many others that are described in the work of Nordenstrom, B. E., Biologically Closed Electrical Systems: Clinical, Experimental and Theoretical Evidence of an Additional Circulatory System; Stockholm, Nordic Medical Publications, 1983, and Evans, E. E., Schentag J. J., Jusko W. J. eds, Applied Pharmacoldnetics: Principles of Therapeutic Drug Monitoring, 3rd ed, Vancouver, Wash., 1992, which are incorporated herein by reference.

Dosage forms designed according to the method of this invention are ideal for reaching one compartment from another and provide more direct application of drug to a target area than most conventional dosage forms, particularly those dosage forms that rely on systemic circulation. This allows the dosage form to actually contain a lower dosage of drug, since a higher percentage of drug is delivered to the target area. The drug can also be delivered directly to the target area as needed. Under some conditions where drug substances are transported through membranes, the drugs may become concentrated in the target tissues. In addition, fewer side effects should be expected from dosage forms according to this invention than from systemic dosage forms.

This dosage form will obviate conventional delivery systems such as nasal sprays. It is superior to such systems because it can be targeted to specific tissues in the body according to the prevailing Donnan Equilibrium of that tissue. These equilibria can be mapped. A Donnan Equilibrium is an area of fixed charge, held in place by the tertiary and quaternary struture of the constituent proteins in the target tissue. Thus a drug can be guided to a specific tisssue and leave another relatively or entirely untouched.

This method is applicable to almost any therapeutic agent that is capable of existing in ionized form, although those agents of lower molecular weight or size will be transported faster and are therefore preferred. Non-ionic agents require an ionizable carrier, which must meet the further requirements of providing for favorable release of the drug at the target site as well as being metabolizable or otherwise easily eliminated physiologically.

OBJECTS OF THE INVENTION

It is an object of the present invention to provide for the design of pharmaceutical compositions which provide better, non-systemic delivery of drugs from a repository compartment of the human body to an adjacent compartment by utilization of the naturally occuring pH gradients between, the two compartments.

It is another object of the present invention to provide a pharmaceutical composition designed in consideration of the Teorell-Meyer gradient for the delivery of a drug from the mouth to the naso-pharyngeal area.

It is a further object of the invention to provide a method of non-systemic administration of an active drug or pro-drug to a patient.

Additional objects of the invention will become evident by study of the detailed description of preferred embodiments of the invention.

SUMMARY OF THE INVENTION

The above and other objects of the invention are provided by a method for formulating the composition of drug dosage forms which will deliver active drugs from a body compartment or organ in which it is placed, i.e., a repository compartment or organ, to a recipient compartment based on the Teorell-Meyer gradient of differing pHs between the two compartments. The method entails identifying both the repository and recipient compartments and determing the pH of each compartment, and is applicable to compartments that are adjacent or contiguous, or that are separated only by a thin membrane. In addition, the repository compartment is in the form of a cavity large enough to contain the desired doage form. Examples of such contiguous compartments include; the mouth and naso-pharynx, mouth-trachea-bronchioles and bronchi, and possibly lung, the surface of the eye, the sclera, the cornea, the anterior chamber, iris, posterior chamber, retina and possibly the optic nerve, the vagina-uterous-fallopian tubes and possibly the ovary, the middle and inner ear, epidural space-meninges-brain, to name a few. The method is also applicable to solid organs as well, such as the eye, liver and prostate. This invention is not limited in scope to the few compartment systems or organs listed here, but is meant to include any such compartment system as meets the basic requirements described herein. Such compartment systems may also be identified in Nordenstrom or Evans. Also, it is expected that a medical or pharmaceutical practitioner of ordinary skill in the art would appreciate the full range of applicability of the within invention.

Selection of contiguous repository/recipient compartment systems to which this invention would apply is dictated largely by pH differences between the two compartments, although other factors may be present as well. Generally, a difference of at least 0.1 pH units between the compartments is necessary, although the larger the pH difference the faster the active drug will be transported. A pH difference of 2.0 pH units is usually preferred, but a larger difference is possible according to the tolerance of the tissues. Thus, each dosage form has its own limits based on the practical pH difference between the compartments and each dosage form should be calculated according to the desired transport time that makes sense for the system. In the preferred embodiment of the mouth—nose system, the transport time should be within the twenty minutes needed to dissolve a typical lozenge. The pH difference, therfore, need only be about 0.4. On the other hand, for a suppository, a pH difference of 0.1 producing a transport time of about an hour and fifteen minutes would be acceptable.

Once the compartment system is identified the active drug or pro-drug must be selected. Transfer by the within method is applicable to almost any drug that is in anionic, cationic or ionizable form. Ionic drugs should be hydrated. Non-ionic drugs may also be used as they can be released from an ionizable carrier such as cyclic carbohydrates and cyclodextrans. The speed of travel of the drug depends on the charge, the atomic or molecular diameter, the molecular weight and the viscosity of the medium in which it travels. The dosage form will move any ionic substance with a molecular weight of up to thousands of Daltons.

In the case of a cationic (positively charged) or acid drug, the repository compartment must have an induced pH substantially lower that the recipient compartment. Conversely, for an anionic (negatively charged) or basic drug the repository compartment must have an induced pH higher than the recipient compartment. Thus, the selection of the buffering system for the dosage form is highly significant. The range of buffers employed correspond to the range of pHs found in the human body, the lowest pH presently known is that of the stomach which is about pH 0.1, the highest pH presently known is about 9.0 and is found in the lower intestine. The buffer or buffer system must last long enough for consumption of the entire dose for complete drug transport to occur. For example, for a typical lozenge of 5 gm, about 20 minutes is necessary.

While the buffers selected must create a pH differential between; the compartments of ideally 2.0 pH units or more to cause rapid drug movement, greater or smaller pH differences are not beyond the scope of this invention. However, when selecting the buffer physiological considerations must also be taken into account. That is, the amount of pH difference between the dosage buffer and the repository compartment that the tissue of that compartment will tolerate.

For the purpose of this invention, the 20 physiologically accepted amino acids and their congeners (e.g., orotic acid, carnitine, ornitine) are generally preferred. The buffers systems usually contain at least two components: a salt and its correlative acid, or base. Buffers may be single compounds in certain cases, such as solutions of amino acids, Tris®, and other compounds containing both acid and basic groups on the same molecule. A buffering system may be complex, containing several components. It may also contain non-related salts and amino acids or similar zwitterionic compounds.

The buffering agent should be able to reliably buffer at the chosen pH, which may be anywhere within the physiological range, so as to preferably maintain a difference of at least 2 pH units between the repository and recipient compartments, according to tissue tolerance, for the preferred embodiment of the invention, to exert substantial buffering capacity within this range. Preferred buffering agents are the amino acids, hydrogen and dihydrogen phosphates, such as sodium dihydrogen phosphate and mixtures of sodium dihydrogen phosphate with sodium hydrogen phosphate, calcium tetrahydrogen phosphate, citric acid and mixtures of citric acid and its monosodium salt, fumaric acid and its monosodium salt, adipic acid and its monosodium salt, tartaric acid and its monosodium salt, ascorbic acid and its monosodium salt, glutamic acid, aspartic acid, betaine hydrochloride, hydrochlorides of amino acids, such as arginine monohydrochloride and glutamic acid hydrochloride and saccharic acid, and other suitable GRAS ingredients herein incorporated by reference.

According to the invention there is provided a method of designing the dosage form of the composition according to the invention, said method comprising the following steps:

selecting the recipient compartment and the associated repository compartment for placement of the drug dosage form, determining the pHs of both the repository and recipient body compartments, identifying the ion, drug or pro-drug to be used in treatment of the recipient compartment, including the ionic characteristics of the drug and its molecular size and shape, selecting a buffering system that will provide satisfactorily lasting buffering effect in the repository compartment of generally at least 0.1 pH units and preferably 2.0 pH units or more lower than the recipient compartment if the drug is cationic (overall positive charge), or at least 0.1 pH units and preferably 2.0 pH units or more higher than the recipient compartment if the drug is anionic (overall negative charge), and admixing the ion, drug or pro-drug together with the components of the selected buffering system, at least one pharmaceutically acceptable carrier, if needed for the transport of a non-ionic molecule, a pharmaceutically appropriated form base and inert ingredients into a desired dosage form such as a lozenge, tablet, capsule, emulsion, injectable emulsion, implantable seed, physiological insert, ophthalmic insert, absorbable sponges, skin patches, pharmaceutical candles, bougies, troches, pastilles and medicated confections.

In another application of the within invention it is desirable to assess the total drug delivery time between the compartments of a given system in order to determine the necessary pH differences between the compartments. Selecting an appropriate drug delivery time and knowing the pH of the recipient compartment, the pH of the repository compartment necessary for total drug transport can be determined. Accordingly, a buffer system designed to produce this pH can be selected.

The invention further relates to a method for administration of a single dose of a dosage form designed according to the above method to a patient comprising administering orally to the patient a lozenge, capsule, tablet containing a pharmacologically effective amount of an ion, drug or pro-drug in the dosage form created according to this invention.

DETAILED DESCRIPTION

Figure 1:
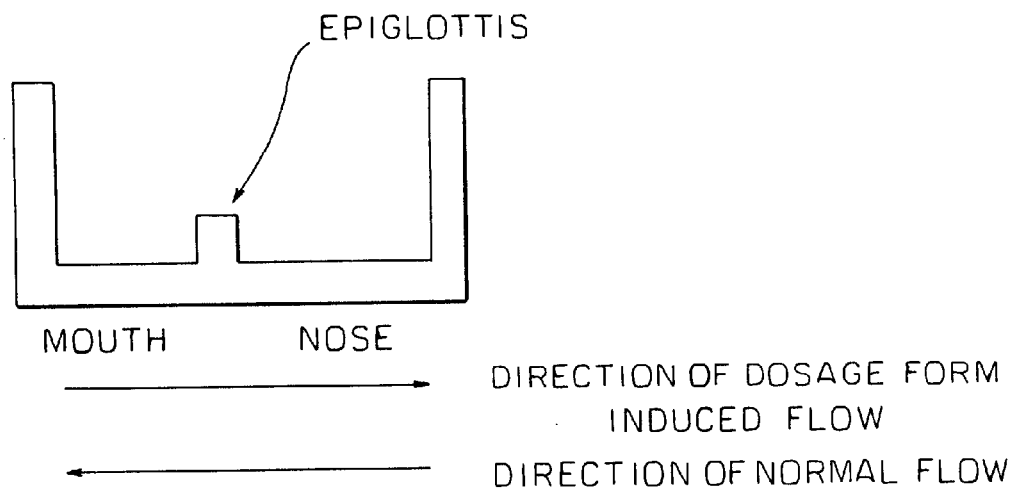
FIG. 1 is a schematic representation of the mouth-nose compartment system.

Any closed or open system of two connected anatomical compartments or cavities lying adjacent to one another having osmotic, charge and concentration differences may be treated with this dosage form. The compartments may be separated by a thin membrane or otherwise connected by a continuous sheet of tissue, or both. Hydro-osmotic pressure, concentration and pH differences between the compartments form a Teorell-Meyer flux gradient. A Teorell-Meyer flux gradient occurs if there is a two or more compartment unit in which different concentrations, relative charges, and hydro-osmotic pressure exist There may be one or more ionic substances or electrolytes present, and the method is dependant on total relative force rather than any single element. Tlus, the driving force for this dosage form depends on the sum of three vector force components: chemical and electrical force and hydro-osmotic pressure.

Therefore, the method or process allows, to the maximum extent possible, the alignment of the three Teorell—Meyer forces in the desired direction of ionic motion. This provides a mechanism to move compounds from compartment to compartment on the bases of all three forces and not just any one or two.

Since the vast majority, if not all, small molecules have diffusion coefficients of similar magnitudes transport across tissue membranes and sheets will be similar. In the analysis that follows, the following definitions apply:

F is the Faraday constant;
P is the permeability coefficient;
Pf(Em) is the potential difference;
f(Em) is a function of the electromotive force, Em is the electromotive force;
R is the universal gas constant;
T is the absolute temperature;
$K_{eq}$ is the equilibrium constant;
C is concentration;
$C_o$ is the initial concentration;
D is the diffusion constant/coeficient
$\mu$ is the mobility coefficient;
$\beta$ is the lipid partition coefficient;
$\delta$ is the distance across the membrane;
q is the absolute value of the electronic charge ($1.602 \times 10^{-19}$ Coulombs;
k is the Boltzman constant; and
z is the valence of the ion.

In non-steady state cases, the hydro-osmotic pressure must be taken into acccount, and in such cases it also provides an additive force. For steady state analysis, the general flux equation in its simplest form is:

$$J = Pf(Em)[C_o - C_o e^{(EmF/RT)}] \quad (1)$$

and, for traversing a membrane; where $$P = \frac{U\beta RT}{\delta F}$$

$$J = -D\,dC/dx = \frac{U\beta Em}{\delta F}[C_o - C_o e^{(EmF/RT)}] \quad (2)$$

See Sperelakis, N., ed. Cell Physiology Source Book, Academic Press, New York, 1995, pp. 61–66. Now, if f(Em)=Em F/RT, and P=−D/dx, and the Boltzman expression for the potential is Em=d$\phi$=−2.303 kT/zq, then $$J = -D\,dC/dX = \frac{-2.6 D \log K_{eq}}{zdx}[C_o - C_o e^{(-2.6 \log Keq)}] \quad (3)$$

For a cation, $K_{eq}$=[products]/[reactants]={oxidized}/{reduced}, then $$J = -D\,dC/dX \quad (4)$$

$$= \frac{-2.6\,D\log[\{oxidized\}/\{reduced\}]}{zdx}$$

$$[C_o - C_o e^{(-2.6\log[\{oxidized\}/\{reduced\}])}]$$

for the steady state. This flux derivation shows that by arranging the equilibrium constant to advantage and by proper buffering, we can change the flux direction.

In the preferred embodiment of the mouth-nose compartment system, fluids, saliva and other liquid and semi-solid substances are directed by the natural action of teeth, tongue and saliva flow in the direction of the digestive system, unless forcibly expelled. Similarly, the fluids of the nose, if not propelled toward the nostrils by expulsed air, will be propelled backwards to the top of the soft palette and from thence to the digestive system. However, according to this invention, pH, electrical and other forces combine in causing reversal of the natural flow of ions from nose to mouth. The contribution made by the electrical potential force is evaluated using the Boltzmann equation;

$$d\phi = 2.303\ kT/zq\ \log K_{eq} \quad (5)$$

and $$Em = \frac{-61.5 \times 10^{-3}}{z}[\log K_{eq}] \quad (6)$$

where z=valence of the ion. Since $K_{eq}$=[products]/[reactants]={oxidized}/{reduced}, by substitution $$Em = \frac{-0.0615\ \text{volts}}{z}\log\{[\text{oxidized}]/[\text{reduced}]\} \quad (7)$$

Since z for H⁺ is one (1), we may calculate, using the average figures in Table 1, using the Boltzmann equation;

$$E_{nose\ to\ mouth} = -0.0615 \times \log\{[10^{-6}[/]10^{-7.2}]\} \quad (8)$$

$$E_{nose\ to\ mouth} = -7.812 \times 10^{-2}\ \text{volts} \quad (9)$$

$$\text{or } E_{mouth\ to\ nose} = +7.812 \times 10^{-2}\ \text{volts} \quad (10)$$

This result may be substituted into the flux equation above, to calculate the actual movement of ions. To examine the flux of [H⁺] in the naso-pharaynx, we can calculate as follows:

$$J_{H+} = D\frac{-2.6\log[\text{Nose}]/[\text{Mouth}]}{dx}\{C_{nose} - C_{mouth}e^{-2.6\log[Nose/Mouth]}\} \quad (11)$$

$$\text{or } J_{H+} = 3.208 \times 10^{-8}\ \text{mole cm/l sec} \quad (12)$$

This result is consistent with a highly stable gradient, a Donnan Potential and equilibrium. This is what would be expected in this area normally.

PREFERRED EMBODIMENT

The invention will now be described in greater detail by reference to the mouth and nose. The naso-pharyngeal cavities can be modeled as a two compartment Teorell-Meyer flux gradient lined with a mucous sheet, whose mid-point can be considered the epiglottis. The tongue and the inferior sides of the soft and hard palettes can be considered the limits of the lower compartment, and the superior side of the soft and hard palettes and the superior structures of the nose can be considered the limits of the upper compartment. See FIG. 1 In the case of the nose-mouth biologic circuit, the epiglottis may act as a "membrane" because of its position and the differing viscosities and concentrations on the superior and inferior sides.

It is readily apparent from FIG. 1 that there are several openings in, this system, and that it is not closed. Among these openings are the mouth, the nostrils, the Eustachean tubes, the tracheal and esophageal openings. Thus the system is not thermodynamically or chemically closed. Because the calculated [H+] flux is very slow, it may be treated as a closed system for the analysis of ion movement within its own area.

Electrically, the flow of positively charged ions or substances, before buffering, is from nose to mouth. Thus, charged particles usually flow in this direction, while electrons move in the mouth to nose direction. The electrical current and ionic flow of the nasopharyngeal cavity can be influenced by the contents and pH of the mouth. A dosage form buffered at a suitable pH can cause reversal in the direction of ion movement. This also occurs according to the Teorell-Meyer equation. The choice of a suitably buffered dosage form will cause either an anion or cation to travel across the membranes of the mouth and into the nose.

Table 1 gives the literature pH ranges for the nose and mouth.

TABLE 1

| pH | Normal pH Values in the Nose and Mouth | | |
|---|---|---|---|
| | Range | Average | [H+] |
| Saliva/Mouth | 6.9–7.5 | 7.2 | $10^{-7.2}$ |
| Nose | 5.5–6.5 | 6.0 | $10^{-6}$ |

By either raising or lowering the pH of the mouth to a suitable extent, by using a lozenge buffered at a correct pH, for example, the ion, ionized drug or pro-drug will be moved electro-osmotically from the mouth to the nose. Generally, a difference of pH of 0.1 to 2.0 is sufficient to cause the transport of most ions or drugs in a reasonable time, but this is not always applicable. In that circumstance, the difference in pH may be increased by a calculable amount based on a reasonable transport time, as discussed below.

As shown above for protons, the naso-pharyngeal cavity may be modeled electrically as a Teorell-Meyer flux gradient for the introduced ions. Referring to FIG. 1, an example is specified for the A++ ion, and assumes the introduction of a dosage form containing the Lewis acid $A^{+2}$. Assuming an average of 20 mls of saliva, a release of the A++ ion from the dosage form into the mouth of greater than 90%, and a lowered mouth pH of 5.25, for the Teorell-Meyer flux gradient formed, the following is observed:

$$/A^0/A^{+2}[1.636 \times 10^{-2}] // A^{+2}[1.683 \times 10^{-5}]/A^0/ \quad (13)$$

(mouth)       (nose)

where; hypothetical plasma A++=110 micrograms/dl= $1.683 \times 10^{-5}$ moles/liter, and dosage form A++ in saliva= $1.636 \times 10^{-2}$ moles/liter. For the hydrogen ion, E can be calculated $$E_{mouth\ to\ nose} = -5.430 \times 10^{-2}\ \text{volts} \quad (14)$$

For the A++ ion, $$E_{mouth\ to\ nose} = -0.0615/2 \times \text{Log}[(1.636 \times 10^{-2})]/[(1.683 \times 10^{-5})] \quad (15)$$

$$E_{mouth\ to\ nose} = -9.19 \times 10^{-2}\ \text{volts}, \quad (16)$$

and the flux for A++

$$J_{H+} = (0.74 \times 10^{-2}\ \text{cm}^2/14\ \text{cm})(-3.9)\{1.57 \times 10^{-2}\} \quad (17)$$

$$J_{H+} = -3.23 \times 10^{-8}\ \text{cm-mole/sec}^{-1} = 0.127\ \text{cm-mg/min}^{-1} \quad (18)$$

$$\text{and } J_{H+} = 2.54\ \text{mg/l-cm over 20 minutes.} \quad (19)$$

It is readily seen that the introduction of an A++ containing dosage form into the mouth, which is buffered to pH 5.25, reverses the current flows against the normal physiological direction. This potential is at least $-9.19 \times 10^{-2}$ volts and may be as much as $-12.21 \times 10^{-2}$ volts, if the hydorgen ion current vector is added. When these are substituted into the flux equation, and the work terms due to the putative hydrostatic/osmotic and mass action gradients are vector added, the effect is most powerful. If the dosage form is buffered at an ever lower pH, the the effect is compounded.

Therefore, the Teorell-Meyer flux gradient, as exemplified in equation (4), will allow electrophoretic motion of ions or ionized compounds in the mouth to nose direction, if the ratio of the concentrations of ions in the mouth to nose is correct. Thus, for the concentration of a cation or an anion:

for a cation pH mouth<<pH nose; and for an anion pH mouth>>nose.

A map of any body cavity, such as the nose—mouth system, where such a concentration gradient exists, may be made to show the Donnan Equilibrium. Since the tissues of the nose and mouth are either positively or negatively charged, a different formulation of dosage form would be required to reach specific tissues, for a specifically charged drug. A Pro-drug synthesis can be applied to the design of such compounds. Carrier/facilitator molecules such as the smaller amino acids, aldehydes, sugars and amino-sugars, and related polysaccharides and other polymeric compounds can be used. Such molecules can buffer, help change pH conveniently, and help propel the desired drug to its site of action, as well as change the pH of the drug.

The time necessary for a charged molecule or ion to arrive at the site of action can be calculated using the information in FIG. 1 and using Newton's Law of Force and Viscosity, defined as:

$$F = NA \, dV/dX \tag{20}$$

where F=force;

N=Newtonian viscosity;

A=area;

dV=change in velocity of ion or molecule;

dX=change of distance; and

V=dX/dT;

V=velocity; and dT=change of time.

Then, $$FdX/NA = dV \tag{21}$$

$$F/NA \int dX = \int dV \tag{22}$$

by integration, force, viscosity and area being constants, we obtain FX/NA=V, and by substitution of dx/dt for V;

$$FX/NA = dX/dT \tag{23}$$

$$\text{and } NAdX/FX = dT. \tag{24}$$

Since FxX=W; where W=work, we can write:

$$NA/W \int dx = \int dT; \text{ then} \tag{25}$$

$$NAX/W = T. \tag{26}$$

Thus, we can calculate the time course for a given particle, knowing the work done on the particle. The work can be calculated from the Gibb's Free Energy expression which takes into account both the chemical and electrical work available for the particle, $$\Delta G = W = -nFE \tag{27}$$

where;

n is the number of equivalents;

F is the Faraday constant, 26,050 cal/volt-equivalent or 108,933 joule/volt-equivalent;

E is the electromotive force or current calculated by the Boltzmann equation; and R=is the universal gas constant, 1.987 cal/mole-degree or 8.314 joule/mole.

The result of the above can be substitued into Newton's Law of Force and Viscosity to get a time for a particle under electrophoretic movement. Using a metal ion A++, as an example, the electrical and chemical work done on the A++ ion at the aforementioned pH can be expressed under the previously described condition as:

$$W_{A\text{-}chemical \, and \, electrical} = +2 \times 26,050 \text{ cal/volt-equiv.} \times 9.18 \times 10^{-2} \text{ cal/mole} \tag{8}$$

$$W_{A\text{-}chemical \, and \, electrical} = +9.04 \times 10^3 \text{ cal/mole or } 13.226 \times 10^3 \text{ joule/mole} \tag{29}$$

$$\text{And } W_{Total \, system} = +5.328 \times 10^3 \text{ cal/mole nose to mouth direction} \tag{30}$$

$$\text{or} = -5.328 \times 10^3 \text{ cal/mole mouth to nose direction} \tag{31}$$

Since the work of the system is negative in the mouth to nose direction, the current ionic flows are reversed because of the introduction of the electro-osmotic dosage form and its lowering of the mouth pH. This is also shown by the Teorell-Meyer flux gradient equation (11), above.

Based on the chemical and electrical work of the system calculated from equation (27), the necessary pH of the repository compartment may be determined for a selected transport time for delivery of the total drug dose. From equation (26), T=NAX/W where W=2.303Rt log[mouth]/[nose].

Given that $$\frac{[\text{oxidized}]}{[\text{reduced}]} = \frac{\text{mouth}}{\text{nose}} = \frac{[\text{repository}]}{[\text{recipient}]} \tag{32}$$

where [ ]=moles/l of a Lewis acid then $$W = 2.303Rt \, \log[\text{mouth}]/[\text{nose}] \quad \text{and} \tag{33}$$

$$W = 2.303Rt \, \log[\text{repository}]/[\text{recipient}]$$

where t=absolute temperature. Thus, the pH of the repository compartment can be expressed as;

$$\log[\text{repository}] = \frac{NAX}{(T)(2.303Rt)} + \log[\text{recipient}] = -pH_{(repository)} \tag{34}$$

The tranport time "T," being selected according to the system intended, the pH of the repository compartment that is produced by the buffer can be calculated.

Figure 2:
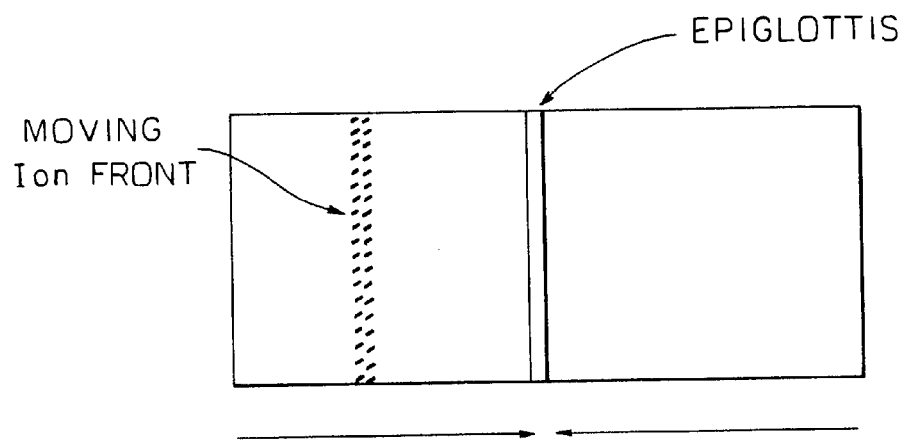
FIG. 2 represents the mouth-nose system as an electrophoretic sheet.

Using the model as provided in FIG. 1 in two-dimensional form, the naso-pharyngeal model is represented as an electrophoretic sheet, FIG. 2. FIG. 2 allows one to consider the naso-pharynx as a flat sheet and apply equation (26). As the average dimension of the mouth is 7 cm and the nose is 7 cm, the total path in the direction of dosage flow is 14 cm, and $$E_{A++dosage \, form} = -12.21 \times 10^{-2} \text{ volts mouth to nose, and}$$

$$W_{A++dosage \, form} = -5.328 \times 10^{-3} \text{ cal/mole ion or } -22.292 \times 10^{-2} \text{ joules/mole-ion, or}$$

$$= -8.846 \times 10^{-21} \text{ cal/ion or } -37.012 \times 10^{-21} \text{ joules/ion.}$$

By assuming the hydrated $A^{++}$ ion to be a sphere with a radius $2.3 \times 10^{-10}$ meters, from $A_A = \pi r^2$, the cross-sectional area $$A_A = 5.290 \times 10^{-20} \times 3.1416 = 1.6621 \times 10^{-19} \text{ m}^2.$$

Applying equation (26), $$T = N \frac{2.3268 \times 10^{-14}}{2.1142 \times 10^{-16}} = 1.10 \times 10^2 N \quad (35)$$

if N=1.1, the average viscosity of the saliva/mucous layer, then
T=1.10×10²(1.1)=121 seconds=2 minutes and one second. Thus, if the average viscosity of the sheet in FIG. 2 is N=1.1 dynes-sec/cm², the average measured time to reach the site of action in the nose from the mouth is about 2 minutes. This result is a general class of dosage forms which will move any charged drug or pro-drug from mouth to nose, and is applicable to other areas of the body where charge and concentration gradients exist.

For each compartment system selected and drug delivery path chosen, the upper limit of the delivery time should be calculated to determine whether the selected pH for the repository compartment will provide the desired result. For the mouth—nose circuit, using the above calculation the following values may be obtained, using the hydrogen ion gradient alone and without regard to the medicament ingredient which may contribute on a charge basis:

| pH Difference | Time for path x = 14 cm |
|---|---|
| 0.75 | 604 sec = 10 min. 4 sec. |
| 0.50 | 906 sec = 15 min. 6 sec. |
| 0.40 | 19 min. |
| 0.10 | 1 hr. 15 min. |

What may not be a practical limit for a lozenge, may be an acceptable time for a different dosage form, such as a suppository.

Gravity is of little consequence in the face of electro-osmotic attraction, as shown by the ratio of Coulomb's Law of Electrostatic Force to Newton's Law of Gravity. Using, by way of example, a metal ion A++ and hydrogen ion, Coulombs Law is expressed as:

$$F_e = K q_1 q_2 / r^2 \quad (36)$$

where K=Coulombs constant; $q_1$=charge density of ion one; $q_2$=charge density of ion two and r=the distance between the ions in meters. Newton's Law of Gravity is expressed as:

$$F_g = G m_1 m_2 / r^2 \quad (37)$$

where G=Newton's gravity constant; $m_1$=mass of ion one; $m_2$=mass of ion two and r=the distance between the ions in meters. Dividing equation (36) by equation (37) and substituting the following values:

charge of proton=$1.602 \times 10^{-19}$ coulombs;
charge of A++ ion=$3.204 \times 10^{-19}$ coulombs;
mass of proton=$1.67 \times 10^{-27}$ kg;
mass of A++ ion=$1.092 \times 10^{-25}$ kg;
Coulomb's constant=$9 \times 10^9$ nt-m²/coul²; and
Gravitation constant=$6.67 \times 10^{-11}$ nt-m²/kg, we obtain $$F_e/F_g = 3.798 \times 10^{+34} \quad (38)$$

for the A++ and hydrogen ion pairs. Two protons may also be compared, with similar results:

$$F_e/F_g = 3.1 \times 10^{+35} \quad (39)$$

Thus, the force of electro-osmotic attraction is very much greater than that produced by gravity.

Thus, in the practice of this invention for the preferred embodiment, the following steps must be observed. To move a positively charged (i.e., acid) ion, drug or pro-drug from the mouth to the nose, the mouth pH must be lowered below that of the target or destination area for the drug, i.e., the nose. Conversely, to move a negatively charged (Le., basic) drug, the pH of the mouth is raised above that of the nasal cavity. This movement is osmo-electrophoretic, and the energy is supplied by the Teorell-Meyer concentration gradient between the mouth and nose.

By the method of this invention as applied to treatment of conditions of the naso-pharygeal compartment, almost any FDA or homeopathically approved drug may be moved. The identification of said drugs will be apparent to one of ordinary skill in the art. Protonated amines are Lewis acids and unprotonated carboxyls are Lewis bases. Acid drugs, or H, antagonists, have the following general formula:

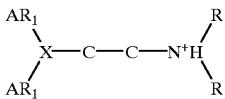

However, by means of example only, some of the more common overall negatively charged drugs (acid drugs) are; Tripelene, Mepyramine, Diphenhydramine, Chlorpheniramine, Astemazole, Terfenadine, Oxatomide, Cyproheptadine, Promethazine, Nidocromyl-Na, Disodium cromoglycate, Carbinoxamine and Buclazine. Cholinergic drugs also fit into this category. Some examples are; Arecholine, Oxytremorine, Choline carbamate (and its derivatives), and Pilocarpine.

The within invention is also applicable to many basic drugs, which can be grouped into families. The lead compound also implies the derivative. Examples of basic drugs, acording to family, are: astringents (the acetate family, where acetate is the active ion), Na Acetate, Al(acetate)₃ (aluminum is also an astringent, but it is an acid. Certain amino acids could move both of them, as a rather large complex); anticonvulsants, such as Phenytoin (Diphenylhydantoin); NSAIDS, such as Tolmetin Na and its family, prostaglandins (wide range of applications, especially for uterine contractions), and prostaglandin F2-alpha and other derivatives of arachidonic acid; antibiotics, especially Cephalosporins and similar compounds, Moxalactam and Azthreonam; anticholinesterase inhibitors (glaucoma-eye), such as Ecothiophate; anti-oncotics, such as Methotrexate and Amethopterin; and retinoic acids such as Tretoin and Isotretoin.

Nonionic drugs must be placed in an ionic carrier molecule (e.g., a steroid coupled with a Cyclo-Dextrin in whose interior a non-ionic substance may be seated by chemical affinity).

Once the destination compartment to be treated is identified, its pH must be determined. Also, the pH of the adjacent compartment must be known so that it will be known to what extent the pH of the adjacent compartment can be altered, as extreme changes in pH cannot always be tolerated. Then, the active drug for treament of an identified conditon must be selected. When this is done, an appropriate dosage may be formulated utilizing an appropriate buffer to modify the pH of the mouth and cause the drug to be transported to the nose.

Using the example of a lozenge to be placed in the mouth for treatment of the nose, formulation of the lozenge must include ingredients which are buffers or buffer pairs or which are capable of maintaining the pH of the lozenge and the mouth at the desired level. Buffers may be single compounds in certain restricted cases, such as solutions of amino acids, Trisg, and other compounds containing both acid and basic groups on the same molecule. Buffers usually are systems containing two components: a salt and its correlative acid or base. However, a buffering system may be complex, containing several components. A multiple component buffer system is a system containing several acids and their correlative salts. It may also contain non-related salts, and amino acids or similar zwitterionic compounds. These acids and salts are usually organic, but may be inorganic. An example if an inorganic physiological buffer is the phosphate buffer system:

Phosphate buffer pairs (sodium, potassium or other ligands) having chemical forms $L_2HPO_4$ $LH_2PO_4$. Carbonate buffers generally have the chemical form $LHCO_3$, where L is a suitable monovalent ion. Zwitterionic compounds can be used, such as all twenty GRAS listed amino acids. Also, GRAS listed acids, aldehydes, sugarts, carbohydrates, substituted carbohydrates or other compounds, alone or in combination, which may be used as buffers or buffer pairs. Artificial buffer systems have also been commercially developed for pharmaceutical use.

EXAMPLE

Based on the above discussions a lozenge may be formulated to be placed in the mouth which would eliminate the need for using nose drops to introduce a therapeutically effective dose of an appropriate medication. For purposes of this example, diphenhydramine and phenylephrine were selected, although other common medicaments for treatment for symptoms of colds, allergies or flu may be used.

In determining the composition of a "hard candy formulation" for a lozenge the hydrochloride salts of diphenhydramine and phenylephrine are preferred because they produce ions in solution according to their disolution profile. It is advantageous to use highly ionizable salts.

| | |
|---|---|
| Phenylephrine = (Phe) | Molecular weight 204 |
| Diphenhydramine = (Diph) | Molecular weight 318 |
| Glycine = (Gly) | Molecular weight 75 |
| Glucose = (Glu) | Molecular weight 198 |

The actual effective doses are to be determined by clinical trial. However, in this example formulation, 50 mg dose of diphenhydramine is chosen. This translates to approximately 0.158 millimoles of diphenhydramine.

In selecting an appropriate lozenge base, the pH of the recipient compartment, the nose, must be considered. Accordingly, the pH of the mouth must be altered by buffering supplied by the lozenge to a pH of approximately 2.0 pH units or more below that of the nose. Thus, the buffering system must alter the pH of the mouth from an average of 7.2 to about 4.8 or so. As amino acids are preferred buffering agents, glycine is an appropriate choice. In this context, glycine serves a double purpose; it serves both as an acid buffer and a complexing carrier agent.

Teorell-Meyer Lozenge Base For an Acid Drug.

To formulate 700 gms of lozenge base, the following are mix together finely comminuted and granular material:

353.92 gms sucrose (50.56%)
83.23 gms fructose (11.89%)
166.46 gms dextrose (23.78%)
96.39 gms glycine (13.77%)

Mix together as finely granulated (10x) powders to make thirty-five (35) twenty gram (20 g) lozenges. To the 696.5 grams of the above lozenge base add 1.75 grams each of diphenhydramine and phenylephrine, a total of 3.5 grams of drug. Compress by standard hot or cold methods.

The amount of glycine, as the buffer, was determined according to this invention to be a large molar excess to insure both pH and complexation of the drug chosen, and based on the average pH of the mouth to be 7.2. The steady state can be approximated by subtracting the first pKa of glycine from that of the mouth (7.2−2.34=4.86). In this example, the base is 13.77% glycine (1.29 moles) and contains 27.54 times more glycine than drug, by weight. This is a molar excess of glycine of 1.28 moles, and 234.5 times the molar amount of drug in the case of diphenhydramine. The buffering action will last as long as the lozenge is incompletely dissolved, and shortly thereafter, until all glycine is neutralized by the homeostatic mechanism of the mouth. This varies from individual to individual, and is on the average about twenty minutes. Using the sperical approximation, the following model applies;

$$dv/dt = 4/3\pi R^2 dR/dt \qquad (40)$$

and the dR/dt term, the decriment in the sphere's diameter with time, varies with time. This time is analogous with dissolution time. Using a spherical model, it can be shown from the flux equation (11) that constant replenishment of the drug occurs is opposition to homeopathic mechanisms in proportion to the change of mass and radius of the lozenge. Therefore, if $$dC = \left(\frac{1}{4/3\pi r^3}\right)\frac{dm}{dr} \qquad (41)$$

the change in concentration is proportional to the change of mass with respect to the radius of the lozenge. This demonstrates that constant replenishment of the initial concentration takes palce at the expense of dm/dr, the change of mass with respect to lozenge radius, and that the amount of material in the steady state can be considered to be the total dose of the lozenge.

As will be apparent to one skilled in the art, various modifications can be made within the scope of the aforesaid description. Such modifications being within the ability of one skilled in the art form a part of the present invention by the appended claims.

I claim:

1. A method of formulating a drug dosage form composition, said method comprising the steps of;

selecting a recipient compartment of the human body for delivery of a drug, and selecting a contiguous repository compartment of the human body for placement of a drug dosage form, determining the pH of both the repository and recipient human body compartments, selecting a therapeutically effective amount of a drug or pro-drug to be used in treatment of the recipient compartment, wherein said drug or pro-drug is selected from the group consisting of cationic, anionic and nonionic drugs or pro-drugs, and wherein when said drug or pro-drug is nonionic, said drug or pro-drug is associated with an ionizable carrier;

selecting a buffering system based on the ionic character, molecular weight and molecular size of said carrier drug or pro-drug that will provide sufficient buffering effect in the repository compartment to provide delivery of a therapeutic amount of drug to the recipient compartment by producing a pH difference between the repository and recipient compartments, wherein the pH of the repository compartment is determined according to the following formula:

$$-pH_{(repository)} = \log[respository] = \frac{NAX}{(T)(2.303Rt)} + \log[recipient]$$

wherein;
pH=pH of the repository compartment with the dosage form in place,
N=the average Newtonian viscosity of the compartments' fluids,
A=the surface area of the repository compartment,
X=the distance the drug is to travel,
T=the transport time selected,
R=the universal gas constant 1.987 cal/mole-degree or 8.314 joule/mole,
t=temperature of the body compartment in absolute degrees—normally 310 degrees Kelvin,
log is the logarithm of the concentration of drug in the repository compartment,
log is the logarithm of the concentration of drug in the recipient compartment; and
wherein said buffering system is capable of sustaining the pH difference in the repository compartment for a period of time sufficient for delivery of the carrier drug or pro-drug to the recipient compartment,
admixing the therapeutically effective amount of the ion, drug or pro-drug together with the components of the selected buffering system, a pharmaceutically appropriate form base and inert ingredients into a desired dosage form.

2. The method according to claim 1, wherein the buffering system is selected to produce a pH in the repository compartment of at least 0.1 pH units difference than the pH of the recipient compartment.

3. The method according to claim 2 wherein the carrier, drug, or pro-drug selected is anionic and the buffering system is selected to produce a pH in the repository body compartment of at least 0.1 pH units higher than the pH of the recipient body compartment.

4. The method according to claim 3 wherein the buffering system is selected to produce a pH in the repository body compartment to be at least 2.0 pH units higher than the pH of the recipient body compartment.

5. The method according to claim 2 wherein the carrier, drug, or pro-drug selected is cationic and the buffering system is selected to produce a pH in the repository body compartment of at least 0.1 pH units lower than the pH of the recipient body compartment.

6. The method according to claim 5 wherein the recipient compartment selected is the nose, the repository compartment selected is the mouth, the cationic drug is selected from the group consisting of phenylephrine and diphenhydramine and the buffering system is selected to produce a pH in the mouth of about 4.8 or lower.

7. The method according to claim 6 wherein the buffering system selected is glycine.

8. The method according to claim 5 wherein the buffering system is selected to produce a pH in the repository body compartment to be at least 2.0 pH units lower than the pH of the recipient body compartment.

9. The method according to claim 1 wherein the drug or pro-drug selected is nonionic and wherein said drug or pro-drug is further admixed with a pharmaceutically acceptable ionizable carrier, said carrier imparting either an anionic or cationic character to said nonionic drug or pro-drug and allowing for the transport of said nonionic drug or pro-drug to the recipient body compartment.

10. The method according to claim 1 wherein the buffer is selected from the group consisting of physiologically acceptable amino acids and their congeners.

11. A method of formulating a drug dosage form composition, said method comprising the steps of;
selecting a recipient compartment of the human body for delivery of a drug, and selecting a contiguous repository compartment of the human body for placement of a drug dosage form,
determining the pH of both the repository and the recipient human body compartments,
selecting a therapeutically effective amount of a drug or pro-drug to be used in treatment of the recipient compartment, wherein said drug or pro-drug is selected from the group consisting of cationic, anionic and nonionic drugs or pro-drugs, and wherein when said drug or pro-drug is nonionic, said drug or pro-drug is associated with an ionizable carrier, selecting a time in which to deliver the total dosage of drug from the repository compartment to the recipient compartment,
determining the pH of the repository compartment necessary to deliver the therapeutic amount of the selected drug to the recipient compartment within the selected time, according to the expression $$-pH_{(repository)} = \log[respository] = \frac{NAX}{(T)(2.303Rt)} + \log[recipient]$$

wherein;
pH=pH of the repository compartment with the dosage form in place,
N=the average Newtonian viscosity of the compartments' fluids,
A=the surface area of the repository compartment,
X=the distance the drug is to travel,
T=the transport time selected,
R=the universal gas constant 1.987 cal/mole-degree or 8.314 joule/mole,
t=temperature of the body compartment in absolute degrees—normally 310 degrees Kelvin,
log is the logarithm of the concentration of drug in the repository compartment,
log is the logarithm of the concentration of drug in the recipient compartment; and
selecting a buffering system that will provide sufficient buffering effect in the repository compartment to produce the pH value determined with respect to the time for total drug delivery, and
admixing the therapeutically effective amount of the carrier drug or pro-drug together with the components of the selected buffering system, a pharmaceutically appropriate base and inert ingredients into a desired dosage form.

12. A dosage form for the delivery of a therapeutically effective amount of a drug or pro-drug from one anatomical compartment to a contiguous anatomical compartment, said dosage form being designed by the steps of:
selecting a recipient compartment of the human body for delivery of a drug, and selecting a contiguous repository compartment of the human body for placement of a drug dosage form,
determining the pH of both the repository and recipient human body compartments, selecting a therapeutically effective amount of a drug or pro-drug to be used in treatment of the recipient compartment, wherein said drug or pro-drug is selected from the group consisting of cationic, anionic and nonionic drugs or pro-drugs, and wherein when said drug or pro-drug is nonionic, said drug or pro-drug is associated with an ionizable carrier, wherein the pH of the repository compartment necessary to allow an effective amount of the drug according to the formula:

$$-pH_{(repository)} = \log[respository] = \frac{NAX}{(T)(2.303Rt)} + \log[recipient]$$

wherein;
pH=pH of the repository compartment with the dosage form in place,
N=the average Newtonian viscosity of the compartments' fluids,
A=the surface area of the repository compartment,
X=the distance the drug is to travel,
T=the transport time selected,
R=the universal gas constant 1.987 cal/mole-degree or 8.314 joule/mole, and
log is the logarithm of the concentration of drug in the repository compartment,
log is the logarithm of the concentration of drug in the recipient compartment,
t=temperature of the body compartment in absolute degrees—normally 310 degrees Kelvin;
selecting a buffering system based on the ionic character, molecular weight and molecular size of said carrier drug or pro-drug that will provide sufficient buffering effect in the repository compartment to provide delivery of a therapeutic amount of drug to the recipient compartment by producing a pH difference between the repository and recipient compartments, wherein said buffering system is capable of sustaining the pH difference in the repository compartment for a period of time sufficient for delivery of the drug or pro-drug to the recipient compartment,
admixing the therapeutically effective amount of the drug or pro-drug together with the components of the selected buffering system, a pharmaceutically appropriate base and inert ingredients into a desired dosage form.

13. The dosage form according to claim 12, wherein the buffering system is selected to produce a pH in the repository compartment of at least 0.1 pH units difference than the pH of the recipient compartment.

14. A dosage form according to claim 13 wherein the carrier, drug, or pro-drug selected is anionic and the buffering system is selected to produce a pH in the repository body compartment of at least 0.1 pH units higher than the pH of the recipient body compartment.

15. A dosage form according to claim 14 wherein the ion, drug or pro-drug selected is anionic and the buffering system is selected to produce a pH in the repository body compartment of at least 2.0 pH units higher than the pH of the recipient body compartment.

16. A dosage form according to claim 13 wherein the carrier, drug, or pro-drug selected is cationic and the buffering system is selected to produce a pH in the repository body compartment of at least 0.1 pH units lower than the pH of the recipient body compartment.

17. A dosage form according to claim 16 wherein the recipient compartment selected is the nose, the repository compartment selected is the mouth, the cationic drug is selected from the group consisting of phenylephrine and diphenhydramine and the buffering system is selected to produce a pH in the mouth of about 4.8 or lower.

18. A dosage form according to claim 17 wherein the buffering system selected is glycine.

19. A dosage form according to claim 16 wherein the ion, drug or pro-drug selected is cationic and the buffering system is selected to produce a pH in the repository body compartment of at least 2.0 pH units lower than the pH of the recipient body compartment.

20. A dosage form according to claim 12 wherein the drug or pro-drug selected is nonionic and wherein said drug or pro-drug is further admixed with a pharmaceutically acceptable ionizable carrier, said carrier imparting either an anionic or cationic character to said nonionic drug or pro-drug and allowing for the transport of said nonionic drug or pro-drug to the recipient body compartment.

21. The dosage form according to claim 12 wherein the buffer is selected from the group consisting of physiologically acceptable amino acids and their congeners.

22. A method for delivering a therapeutically effective amount of drug to a recipient anatomical compartment of the human body comprising the steps of;
selecting a contiguous repository compartment of the human body for placement of a drug dosage form,
placing in the repository compartment a drug dosage form containing a therapeutically effective amount of the drug to be delivered, said drug dosage form being formulated according to a method comprising the following steps;
determining the pH of both the repository and recipient human body compartments,
determining the pH the repository compartment necessary to deliver the therapeutic amount of the drug to the recipient compartment within the selected time according to the formula:

$$-pH_{(repository)} = \log[respository] = \frac{NAX}{(T)(2.303Rt)} + \log[recipient]$$

wherein;
pH=pH of the repository compartment with the dosage form in place,
N=the average Newtonian viscosity of the compartments' fluids,
A=the surface area of the repository compartment,
X=the distance the drug is to travel,
T=the transport time selected,
R=the universal gas constant 1.987 cal/mole-degree or 8.314 joule/mole, and
log is the logarithm of the concentration of drug in the repository compartment,
log is the logarithm of the concentration of drug in the recipient compartment,
t=temperature of the body compartment in absolute degrees—normally 310 degrees Kelvin;
selecting a therapeutically effective amount of a drug or pro-drug to be used in treatment of the recipient compartment, wherein said drug or pro-drug is selected from the group consisting of cationic, anionic and nonionic drugs and pro-drugs, and wherein when said drug or pro-drug is nonionic, said drug or pro-drug is associated with an ionizable carrier
selecting a buffering system based on the ionic character, molecular weight and molecular size of said carrier drug or pro-drug that will provide sufficient buffering effect in the repository compartment to provide delivery of a therapeutic amount of drug to the recipient compartment by producing a pH difference between the repository and recipient compartments, wherein said buffering system is capable of sustaining the pH difference in the repository compartment for a period of time sufficient for delivery of the carrier drug or pro-drug to the recipient compartment, admixing the therapeutically effective amount of the carrier drug or pro-drug together with the compartments of the selected buffering system, a pharmaceutically appropriate form base and inert ingredients into a desired dosage form.

23. The method according to claim 22, wherein the buffering system is selected to produce a pH in the repository compartment of at least 0.1 pH units difference than the pH of the recipient compartment.

24. The method according to claim 23 wherein the carrier, drug, or pro-drug selected is anionic and the buffering system is selected to produce a pH in the repository body compartment of at least 0.1 pH units higher than the pH of the recipient body compartment.

25. The method according to claim 24 wherein the buffering system is selected to produce a pH in the repository body compartment of at least 2.0 pH units higher than the pH of the recipient body compartment.

26. The method according to claim 23 wherein the carrier, drug, or pro-drug selected is cationic and the buffering system is selected to produce a pH in the repository body compartment of at least 0.1 pH units lower than the pH of the recipient body compartment.

27. The method according to claim 26 wherein the recipient compartment selected is the nose, the repository compartment selected is the mouth, the cationic drug is selected from the group consisting of phenylephrine and diphenhydramine and the buffering system is selected to produce a pH in the mouth of about 4.8 or lower.

28. The method according to claim 27 wherein the buffering system selected is glycine.

29. The method according to claim 26 wherein the buffering system is selected to produce a pH in the repository body compartment of at least 2.0 pH units lower than the pH of the recipient body compartment.

30. The method according to claim 22 wherein the drug or pro-drug selected is nonionic and wherein said drug or pro-drug is further admixed with a pharmaceutically acceptable ionizable carrier, said carrier imparting either an anionic or cationic character to said nonionic drug or pro-drug and allowing for the transport of said nonionic drug or pro-drug to the recipient body compartment.

* * * * *

UNITED STATES PATENT AND TRADEMARK OFFICE
CERTIFICATE OF CORRECTION

PATENT NO. : 6,414,033 B1
DATED : July 2, 2002
INVENTOR(S) : Nicholas Secusa

It is certified that error appears in the above-identified patent and that said Letters Patent is hereby corrected as shown below:

Column 6,
Lines 28-34, delete Equation (4) and insert therefor $$-- J = -DdC/dX = \frac{-2.6D\text{Log}[\{\text{oxidized}\}/\{\text{reduced}\}]}{zdx}[C_0 - C_0 e^{(-2.6\text{Log}[\{\text{oxidized}\}/\{\text{reduced}\}])}] \quad (4) --$$

Column 8,
Line 49, Equation (17) delete "$J_{H+}$" and insert therefor -- $J_{A++}=$ --
Line 51, Equation (18) delete "$J_{H+}$" and insert therefor -- $J_{A++}=$ --
Line 53, Equation (19) delete "$J_{H+}$" and insert therefor -- $J_{A++}=$ --

Column 10,
Line 7, delete "(8)" and insert therefor -- (28) --
Line 11, delete "$W_{Total\ system}$" and insert therefor -- $W_{Total\ system\ chemical\ \&\ electrical\ work}$ --
Line 64, delete "$A_A=\pi r^2$" and insert therefor -- $A=\pi r^2$ --
Line 67, delete "$A_A=$" and insert therefor -- $A_{++}=$ --

Column 13,
Line 3, delete "Trisg" and insert therefor -- Tris® --
Line 12, delete "if" and insert therefor -- of --
Line 13, delete ":" and insert therefor a period
Line 18, delete "sugarts" and insert therefor -- sugars --

Column 14,
Line 18, delete "sperical" and insert therefor -- spherical --
Line 26, after "occurs", delete "is" and insert therefor -- in --

Signed and Sealed this

Seventh Day of September, 2004

JON W. DUDAS
*Director of the United States Patent and Trademark Office*